United States Patent

Tapolczay et al.

Patent Number: 5,089,510
Date of Patent: Feb. 18, 1992

[54] INSECTICIDES

[75] Inventors: David J. Tapolczay, Lower Early Reading; Vivienne M. Anthony, Maidenhead; John M. Clough, Marlow; Christopher R. A. Godfrey, Bracknell; Paul J. de Fraine, Wokingham, all of England

[73] Assignee: Imperial Chemical Industries PLC, London, United Kingdom

[21] Appl. No.: 446,607

[22] Filed: Dec. 6, 1989

[30] Foreign Application Priority Data

Dec. 7, 1988 [GB] United Kingdom ............... 8828543

[51] Int. Cl.⁵ .............................................. A01N 43/40
[52] U.S. Cl. ..................................... 514/345; 514/350
[58] Field of Search ................................ 514/345, 350

[56] References Cited

FOREIGN PATENT DOCUMENTS 0226917 7/1987 European Pat. Off. .
0278595 8/1988 European Pat. Off. .
0299694 8/1988 European Pat. Off. .
49-007214 2/1974 Japan .

Primary Examiner—Allan J. Robinson
Attorney, Agent, or Firm—Cushman, Darby & Cushman

[57] ABSTRACT

A method of killing or controlling insect, mite or nematode pests which comprises applying to the pest or to the locus thereof an effective amount of a compound of formula (I):

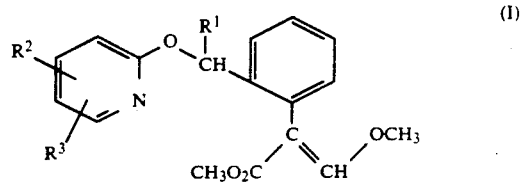

in which $R^1$ is hydrogen or alkyl; $R^2$ is hydrogen, halogen, alkyl, alkoxy, aryl, heteroaryl, arylalkyl, heteroarylalkyl, aryloxy, heteroaryloxy, arylalkenyl, heteroarylalkenyl, aryloxyalkyl, heteroaryloxyalkyl, arylalkoxy, heteroarylalkoxy, $-CO_2R^5$, alkyl$CO_2R^6$, monoalkylamino or dialkylamino; $R^3$ is hydrogen, halogen, alkyl, alkoxy, hydroxy, monoalkylamino, dialkylamino, $-CO_2R^4$ or nitro; and $R^4$, $R^5$ and $R^6$ are hydrogen or alkyl; any of the foregoing aliphatic moieties are optionally substituted with one or more of halogen, hydroxy, alkoxy, or haloalkoxy; any of the foregoing aryl or heteroaryl moieties are optionally substituted with one or more of halogen, alkyl, alkoxy, haloalkyl or haloalkoxy.

4 Claims, No Drawings

INSECTICIDES

The present invention relates to a method of killing or controlling insect, mite or nematode pests and to compositions for use in that method.

European Patent Publications Nos. 0226917 and 0278595 describe a group of propenoic acid derivatives useful as fungicides. It has now been found that certain of these compounds and other related compounds have useful insecticidal, miticidal and nematocidal activity. In addition, the compounds may have knockdown activity against flies and mosquitoes.

According to the present invention there is provided a method of killing or controlling insect, mite or nematode pests which comprises applying to the pest or to the locus thereof an effective amount of a compound of formula (I):

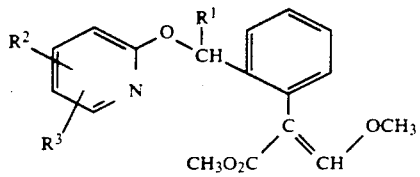

(I)

in which $R^1$ is hydrogen or alkyl; $R^2$ is hydrogen, halogen, alkyl, alkoxy, aryl, heteroaryl, arylalkyl, heteroarylalkyl, aryloxy, heteroaryloxy, arylalkenyl, heteroarylalkenyl, aryloxyalkyl, heteroaryloxyalkyl, arylalkoxy, heteroarylalkoxy, $-CO_2R^5$, alkyl$CO_2R^6$, monoalkylamino or dialkylamino; $R^3$ is hydrogen, alkyl, halogen, alkoxy, hydroxy, monoalkylamino, dialkylamino, $-CO_2R^4$ or nitro; and $R^4$, $R^5$ and $R^6$ are hydrogen or alkyl; any of the foregoing aliphatic moieties are optionally substituted with one or more of halogen, hydroxy, alkoxy or haloalkoxy; any of the foregoing aryl or heteroaryl moieties are optionally substituted with one or more of halogen, alkyl, alkoxy, haloalkyl or haloalkoxy.

The compounds of formula (I) contain a double bond and can, therefore, exist in (E)- or (Z)-isomeric forms. The invention relates to the individual isomers and mixtures thereof in all proportions. Generally the (E)-isomer is the more active and it is preferred that the compounds of formula (I) are in this form.

The term "halogen" used herein includes fluorine, chlorine, bromine and iodine.

Alkyl groups, the alkyl moieties of alkoxy, monoalkylamino, dialkylamino and substituted alkyl groups preferably contain 1 to 6, more preferably 1 to 4, carbon atoms and can be in the form of straight or branched chains. They include methyl, ethyl, n-propyl and t-butyl. Haloalkyl includes chloro- and fluoro($C_{1-4}$)alkyl, especially trifluoromethyl. Suitable optional substituents for the alkyl groups and alkyl moieties of alkoxy, monoalkylamino and dialkylamino include one or more of halogen, hydroxy, alkoxy and haloalkoxy.

The aryl moiety of aryloxy, arylalkenyl, aryloxyalkyl and arylalkyloxy groups and aryl itself includes phenyl, while the heteroaryl moiety of heteroaryloxy, heteroarylalkenyl, heteroaryloxyalkyl and heteroarylalkyloxy groups and heteroaryl itself includes pyridyl and pyrimidinyl. Suitable optional substituents for aryl and heteroaryl groups include one or more of halogen, alkyl, alkoxy, haloalkyl and haloalkoxy.

The alkenyl moiety of arylalkenyl and heteroarylalkenyl groups contains 2 to 6, suitably 2, carbon atoms. Suitable optional substituents for the alkenyl group include one or more of halogen, hydroxy, alkoxy and haloalkoxy.

In one particular aspect the present invention provides a method of killing or controlling insect, mite or nematode pests which comprises applying to the pest or to the locus thereof an effective amount of a compound of formula (I):

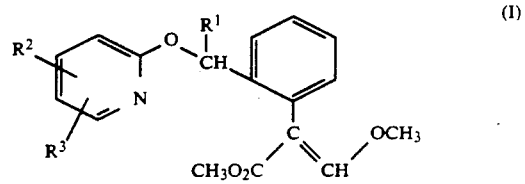

(I)

which $R^1$ is hydrogen or alkyl; $R^2$ is hydrogen, halogen, alkyl, alkoxy, aryl, heteroaryl, arylalkyl, heteroarylalkyl, aryloxy, heteroaryloxy, arylalkenyl, heteroarylalkenyl, aryloxyalkyl, heteroaryloxyalkyl, arylalkoxy, heteroarylalkoxy, $-CO_2R^5$, alkyl$CO_2R^6$, monoalkylamino or dialkylamino; $R^3$ is hydrogen, alkyl, halogen, alkoxy, hydroxy, monoalkylamino, dialkylamino or $-CO_2R_4$; and $R^4$, $R^5$ and $R^6$ are hydrogen or alkyl; any of the foregoing aliphatic moieties are optionally substituted with one or more of halogen, hydroxy, alkoxy or haloalkoxy; any of the foregoing aryl or heteroaryl moieties are optionally substituted with one or more of halogen, alkyl, alkoxy, haloalkyl or haloalkoxy.

In another aspect the compounds used in the method of the invention are those of formula (I) which are in the form of the (E)-isomer.

In yet another aspect the compounds used in the method of the invention are those of formula (I) in which $R^1$ is hydrogen or $C_{1-4}$ alkyl; $R^2$ is hydrogen, halogen, $C_{1-4}$ alkyl, $C_{1-4}$ haloalkyl, hydroxy($C_{1-4}$) alkyl, $C_{1-4}$ alkoxy($C_{1-4}$)alkyl, $C_{1-4}$ haloalkoxy($C_{1-4}$) alkyl, $C_{1-4}$ alkoxy, $C_{1-4}$ haloalkoxy, $-CO_2R^5$, ($C_{1-4}$) alkyl$CO_2R^6$, mono($C_{1-4}$)alkylamino or di($C_{1-4}$) alkylamino; $R^3$ is hydrogen, hydroxy, halogen, $C_{1-4}$ alkyl, $C_{1-4}$ haloalkyl, $C_{1-4}$ alkoxy, $C_{1-4}$ haloalkoxy or $-CO_2R^4$; and $R^4$, $R^5$ and $R^6$ are hydrogen, $C_{1-4}$ alkyl or $C_{1-4}$ haloalkyl.

In a further aspect the compounds used in the method of the invention are those of formula (I) in which $R^1$ is hydrogen; $R^2$ is hydrogen, halogen (especially chlorine and bromine), $C_{1-4}$ alkyl (especially methyl and t-butyl) or $C_{1-4}$ haloalkyl (especially trifluoromethyl); $R^3$ is hydrogen, halogen (especially chlorine) or $C_{1-4}$ haloalkyl (especially trifluoromethyl).

In a still further aspect the compounds used in the method of the invention are those of formula (I) in which $R^1$ is hydrogen, $R^2$ is hydrogen, fluorine, chlorine, bromine, $C_{1-4}$ alkyl or trifluoromethyl; and $R^3$ is hydrogen, chlorine or trifluoromethyl.

In yet another aspect the compounds used in the method of the invention are those of formula (I) in which $R^1$ is hydrogen; $R^2$ is chlorine, bromine, methyl or trifluoromethyl; and $R^3$ is hydrogen or trifluoromethyl.

Examples of compounds of formula (I) are set out in Table I below.

TABLE I

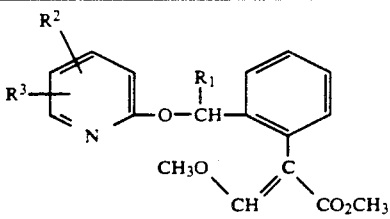

| COMPOUND NO. | $R^1$ | $R^2$ | $R^3$ | ISOMER |
|---|---|---|---|---|
| 1 | H | 6-Cl | H | E |
| 2 | H | 3-CF$_3$ | 6-CF$_3$ | E |
| 3 | H | 6-Br | H | E |
| 4 | H | 4-CF$_3$ | H | E |
| 5 | H | 4-C(CH$_3$)$_3$ | H | E |
| 6 | H | 4-CF$_3$ | 5-Cl | E |
| 7 | H | 6-CH$_3$ | H | E |
| 8 | H | 6-CF$_3$ | H | E |
| 9 | H | H | H | E |
| 10 | H | 5-CF$_3$ | H | E |
| 11 | H | 6-F | H | E |
| 12 | H | 5-CO$_2$C$_2$H$_5$ | H | E |
| 13 | H | 4-CH$_3$ | H | E |
| 14 | H | 3-Br | 5-CF$_3$ | E |
| 15 | H | 3-CH$_3$ | H | E |
| 16 | H | 5-Br | H | E |
| 17 | H | 3-Cl | H | E |
| 18 | H | 3-CH$_3$ | 5-Cl | E |
| 19 | H | 5-CH$_3$ | H | E |
| 20 | H | 6-CH$_3$ | 3-NO$_2$ | E |
| 21 | H | H | 3-NO$_2$ | E |

The compounds of formula (I) can be prepared as described in European Patent Publication No. 0226917 and European Application No. 88300280.0 and the contents of that publication and application in so far as they are relevant to the present invention are incorporated herein by reference.

In order to apply the compounds to the locus of the pests they are usually formulated into compositions which include, in addition to the insecticidally active ingredient or ingredients of formula (I), suitable inert diluent or carrier materials, and/or surface active agents. In another aspect the invention includes such insecticidal compositions.

The compositions may also contain another pesticidal material, for example another insecticide, nematocide or acaricide, or a fungicide, or may also contain an insecticide synergist, such as for example dodecyl imidazole, safroxan, MGK 264 or piperonyl butoxide.

The compositions may be in the form of dusting powders wherin the active ingredient is mixed with a solid diluent or carrier, for example kaolin, bentonite, dieselguhr, or talc, or they may be in the form of granules, wherein the active ingredient is absorbed in a porous granular material for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzensulphonate, sodium, calcium or ammonium lignosulphonate, or butylnapthalene sulphonate, and a mixture of the sodium salts of diisopropyl- and triiso-propylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents. Other suitable organic solvents are dimethyl formamide, ethylene dichloride, isopropyl alcohol, propylene glycol and other glycols, diacetone alcohol, toluene, kerosene, white oil, methylnapthalene, xylenes and trichloroethylene, N-methyl-2-pyrrolidone and tetrahydro furfuryl alcohol (THFA).

The compositions to be used as sprays may also be in the form of aerosols wherein the formulation is held in a container under pressure in the presence of a propellant such as fluorotrichloromethane or dichlorodifluoromethane.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain from 5–95% suitably from 10–85% by weight of the active ingredient or ingredients. When diluted to form aqueous preparations such preparations may contain varying amounts of the active ingredient depending upon the purpose for which they are to be used. For agricultural, horticultural or domestic purposes, an aqueous preparation containing between 0.0001% and 0.1% by weight of the active ingredient is particularly useful.

In use the compositions are applied to the pests or to the locus of the pests, i.e. to the habitat of the pests or to growing plants liable to infestation by the pests, by any of the known means of applying pesticidal compositions, for example, by dusting or spraying, including electro-dynamic spraying.

The above described compositions are active against a range of pests including nematodes.

Rates of application will depend upon a number of factors including the type of pest, degree of infestation, etc. However, in general, application of from 0.5 to 4.0 kg/ha will be appropriate.

The following Examples illustrate the invention.

EXAMPLE 1

The insecticidal properties of the compound of formula (I) were demonstrated as follows :

The activity of the compound was determined using a variety of insect, mite and nematode pests. Except in the case of knockdown activity against *Musca domestica*, where the test procedure is described later, the compound was used in the form of liquid preparations containing from 50 to 1000 parts per million (ppm) by weight of the compound. The preparations were made by dissolving the compound in acetone and diluting the solutions with water containing 0.1% by weight of a wetting agent sold under the trade name "SYNPERONIC" NX until the liquid preparations contained the required concentration of the product. "SYNPERONIC" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to seven days after the treatment.

The results of the tests are given in Table III for each of the products, at the rate in parts per million given in the second column as a grading of mortality designated as 9, 5 or 0 wherein 9 indicates 80–100% mortality (70–100% root-knot reduction as compared with untreated plants for *Meloidogyne incognita* semi in vitro test), 5 indicates 50–79% mortality (50–69% root-knot reduction for *Meloidogyne incognita* semi in vitro test) and 0 indicates less than 50% mortality (root-knot reduction for *Meloidogyne incognita* semi in vitro test).

In Table III the pest organism used is designated by a letter code and the pest species, the support medium or food, and the type and duration of test is given in Table II.

The knockdown properties against *Musca domestica* were demonstrated as follows.

A sample of the compound was diluted in 0.1% ethanol/acetone (50:50 mixture) and made up to either a 1000 ppm or 500 ppm solution with 0.1% aqueous Synperonic NX solution. The solution (1 ml) was then sprayed directly onto ten mixed sex houseflies held in a drinking cup containing a sugar lump which was also sprayed.

Immediately afterspraying the cups were inverted and left to dry. An assessment of knockdown was made when the cups were righted 15 minutes later. The flies were then provided with a damp cotton wool pad, and held for 48 hours in a holding room conditioned at 25° C. and 65% relative humidity before a mortality assessment was made.

TABLE II

| CODE LETTERS (TABLE IV) | TEST SPECIES | SUPPORT MEDIUM/FOOD | TYPE OF TEST | DURATION (days) |
| --- | --- | --- | --- | --- |
| TU AC | *Tetranychus urticae* (spider mite - adult) | French bean leaf | Contact | 3 |
| TU EO | *Tetranychus urticae* (spider mite - egg) | French bean leaf | Contact | 3 |
| TU NG | *Tetranychus urticae* (spider mite - nymph) | French bean leaf | Contact (growth) | 6 |
| MP | *Myzus persicae* (aphid) | Chinese Cabbage leaf | Contact | 3 |
| NC NC | *Nephotettix cincticeps* (green leaf hopper - nymph) | Rice plant | Contact | 2 |
| NC NG | *Nephotettix cincticeps* (green leaf hopper - nymph) | Rice plant | Contact (growth) | 6 |
| MD AK | *Musca domestica* (housefly - adult) | Plastic pot | Contact (knockdown) | 15 mins |
| MD AC | *Musca domestica* (housefly - adult) | Plastic pot | Contact | 3 |
| BG NK | *Blattella germanica* (cockroach nymph) | Plastic pot | Contact (knockdown) | 15 mins |
| BG NC | *Blattella germanica* (cockroach nymph) | Plastic pot | Contact | 2 |
| HV LR | *Heliothis virescens* (tobacco budworm - larva) | Cotton leaf | Residual | 2 |
| HV LG | *Heliothis virescens* (tobacco budworm - larva) | Cotton leaf | Residual (growth) | 5 |
| SP LR | *Spodoptera exigua* (lesser armyworm - larva) | Cotton leaf | Residual | 2 |
| SP LG | *Spodoptera exigua* (lesser armyworm - larva) | Cotton leaf | Residual (growth) | 5 |
| DB | *Diabrotica balteata* (cucumber beetle - larva) | Filter paper/ maize seed | Residual | 2 |
| MI JC | *Meloidogyne incognita* (rootknot nematode - larva) | in vitro | Contact | 1 |

"Contact" tests indicates that both pests and medium were treated and "Residual" indicates that the medium was treated before infestation with the pests

TABLE III

| Compound No | Rate (ppm) | TU AC | TU EO | TU NG | MP | NC NC | NC NG | MD AK | MD AC | BG NK | BG NC | HV LR | HV LG | SP LR | SP LG | DB | MJ JC |
|---|---|---|---|---|---|---|---|---|---|---|---|---|---|---|---|---|---|
| 1 | 1000 | 9 | 0 | 9 | 0 | 9 | | 9 | 0 | 0 | 0 | 0 | 0 | 9 | | 0 | |
|   | 25 | | | | | | | | | | | | | | | | 0 |
| 2 | 1000 | 9 | 0 | 9 | 5 | 9 | | 0 | 0 | 0 | 0 | 5 | 5 | 5 | 9 | 9 | |
|   | 25 | | | | | | | | | | | | | | | | 0 |
| 3 | 1000 | 9 | 5 | 5 | 5 | 9 | | 0 | 5 | 0 | 0 | 0 | 5 | 5 | 9 | 9 | |
|   | 25 | | | | | | | | | | | | | | | | 0 |
| 4 | 1000 | 9 | | | | 0 | 0 | | | 0 | 0 | | | 0 | 0 | 0 | |
|   | 1000 | 9 | | | | 9 | | | | 0 | 0 | | | 0 | 5 | 0 | |
| 5 | 1000 | 9 | 0 | 9 | 0 | 0 | 0 | 0 | 9 | 0 | 0 | 0 | 0 | 0 | 0 | 9 | |
|   | 25 | | | | | | | | | | | | | | | | 0 |
| 6 | 1000 | 9 | 0 | 9 | 0 | 0 | 5 | 0 | 0 | 0 | 0 | 0 | 0 | 0 | 0 | 0 | |
|   | 25 | | | | | | | | | | | | | | | | 0 |
| 7 | 1000 | 0 | 0 | 0 | 0 | 9 | | 0 | 0 | 0 | 0 | 0 | 0 | 0 | 0 | 9 | |
|   | 25 | | | | | | | | | | | | | | | | 0 |
| 8 | 1000 | | 0 | 9 | 9 | | | 5 | 9 | | | 5 | 9 | | | | |
| 9 | 1000 | | | | | | | 0 | 5 | | | | | | | | |
|   | 1000 | | | | | 9 | | | | 0 | 0 | | | 0 | 0 | 9 | |
| 10 | 1000 | 5 | 0 | 0 | 0 | 5 | 5 | 0 | 9 | 0 | 0 | 0 | 0 | | | 0 | |
|   | 25 | | | | | | | | | | | | | | | | 0 |
| 11 | 1000 | 5 | 0 | 9 | 5 | 9 | — | 5 | 5 | 0 | 0 | 0 | 0 | 0 | 0 | 0 | |
|   | 25 | | | | | | | | | | | | | | | | 0 |
| 12 | 1000 | — | 0 | 0 | 0 | 9 | — | 5 | 5 | 0 | 0 | 0 | 0 | 0 | 5 | — | |
|   | 25 | | | | | | | | | | | | | | | | 0 |
| 13 | 1000 | — | 0 | 5 | 0 | 5 | 5 | 5 | 9 | 0 | 0 | 0 | 9 | 0 | 0 | — | |
|   | 25 | | | | | | | | | | | | | | | | 0 |
| 14 | 1000 | 9 | 9 | — | 9 | 9 | — | 9 | 9 | 0 | 0 | 0 | 9 | 9 | — | 5 | |
|   | 25 | | | | | | | | | | | | | | | | 0 |
| 15 | 1000 | 0 | 0 | 0 | 0 | 9 | — | 0 | 0 | 0 | 0 | 0 | 0 | 9 | — | 5 | |
|   | 25 | | | | | | | | | | | | | | | | 0 |
| 16 | 500 | 0 | 0 | 0 | 5 | 0 | 5 | 5 | 9 | 0 | 0 | 0 | 0 | 0 | 0 | 9 | |
|   | 12.5 | | | | | | | | | | | | | | | | 0 |
| 17 | 500 | 9 | 0 | 9 | 5 | 9 | — | 0 | 0 | 0 | 0 | 0 | 5 | 0 | 0 | 9 | |
|   | 12.5 | | | | | | | | | | | | | | | | 0 |
| 18 | 1000 | 9 | 0 | 0 | 0 | 0 | 0 | 5 | 5 | 0 | 0 | 0 | 0 | 9 | — | 0 | |
|   | 25 | | | | | | | | | | | | | | | | 0 |
| 19 | 500 | 0 | 0 | 5 | 0 | 0 | 9 | 9 | 9 | 0 | 0 | 0 | 9 | 0 | 9 | 9 | |
|   | 12.5 | | | | | | | | | | | | | | | | 0 |
| 20 | 500 | 0 | 0 | 0 | 0 | 0 | 0 | 0 | 0 | 0 | 0 | 5 | 5 | 0 | 0 | 0 | |
|   | 12.5 | | | | | | | | | | | | | | | | 0 |
| 21 | 500 | 5 | 0 | 0 | 0 | 0 | 0 | 0 | 0 | 0 | 0 | 0 | 0 | 0 | 5 | 5 | |
|   | 12.5 | | | | | | | | | | | | | | | | 0 |

A blank indicates not tested

I claim:

1. A method of killing or controlling insect or mite pests which comprises applying to the pest or to the infested locus thereof an insecticidally or miticidally effective amount of a compound of formula (I):

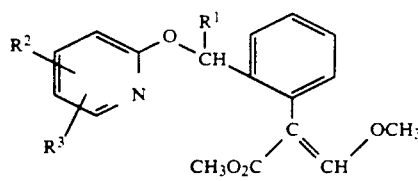

wherein the compound of formula (I) is in the form of the (E)-isomer; and $R^1$ is hydrogen; $R^2$ is hydrogen, halogen, $C_{1-4}$ alkyl, $C_{1-4}$ haloalkyl or $-CO_2R^4$; $R^3$ is hydrogen, halogen or $C_{1-4}$ haloalkyl; and R4 is $C_{1-4}$ alkyl.

2. A method as claimed in claim 1 wherein the compounds used in the method are those of formula (I) in which $R^1$ is hydrogen; $R^2$ is hydrogen, fluorine, chlorine, bromine, $C_{1-4}$ alkyl or trifluoromethyl; and $R^3$ is hydrogen, chlorine or trifluoromethyl.

3. A method as claimed in claim 1 wherein the compounds used in the method are those of formula (I) in which $R^1$ is hydrogen; $R^2$ is chlorine, bromine, methyl or trifluoromethyl; and $R^3$ is hydrogen or trifluoromethyl.

4. A method according to claim 1 wherein $R^1$ is H, $R^2$ is 6-Br and $R^3$ is H.